US00PP36056P2

(12) United States Plant Patent
Wilde

(10) Patent No.: US PP36,056 P2
(45) Date of Patent: Jul. 30, 2024

(54) ***SUTERA* PLANT NAMED 'KLESG22041'**

(50) Latin Name: *Sutera grandiflora*
Varietal Denomination: KLESG22041

(71) Applicant: KLEMM + SOHN GMBH & CO. KG, Stuttgart (DE)

(72) Inventor: Katinka Wilde, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/223,980

(22) Filed: Jul. 19, 2023

(51) Int. Cl.
*A01H 5/02* (2018.01)
*A01H 6/00* (2018.01)

(52) U.S. Cl.
USPC ..... Plt./485
CPC ..... *A01H 6/00* (2018.05)

(58) Field of Classification Search
USPC ..... Plt./485
CPC ..... A01H 5/02
See application file for complete search history.

*Primary Examiner* — Kent L Bell
(74) *Attorney, Agent, or Firm* — Weatherly IP Solutions, LLC; James M. Weatherly

(57) ABSTRACT

A new *Sutera* plant particularly distinguished by having a pink flower color and large flowers is disclosed.

1 Drawing Sheet

Genus and species: *Sutera grandiflora*.
Variety denomination: 'KLESG22041'.

BACKGROUND OF THE NEW PLANT

The present invention comprises a new and distinct variety of *Sutera*, botanically known as *Sutera grandiflora*, and hereinafter referred to by the variety name 'KLESG22041'. 'KLESG22041' originated from a controlled cross-pollination between the proprietary female *Sutera* variety 'SG-2016-0652' (unpatented) and the proprietary male *Sutera* variety 'SG-2016-0692' (unpatented).

From May 2017 through July of 2017 controlled-crosses of the proprietary female *Sutera* variety 'SG-2016-0652' and the proprietary male *Sutera* variety 'SG-2016-0692' were undertaken in a foil house in Stuttgart, Germany and seed was collected in the winter of 2017. In January 2018, seeds were sown and plants were grown for evaluation in Stuttgart, Germany in a greenhouse under glass. A plant line was selected in May 2018 and subsequently named 'KLESG22041'. In May 2018, 'KLESG22041' was first vegetatively propagated in Stuttgart, Germany by asexual cuttings. 'KLESG22041' was found to reproduce true to type in successive generations of asexual propagation via asexual cuttings.

SUMMARY

The following are the most outstanding and distinguishing characteristics of this new variety when grown under normal horticultural practices in Stuttgart, Germany.

1. Pink flower color; and
2. Large flowers.

DESCRIPTION OF THE PHOTOGRAPH

This new *Sutera* plant is illustrated by the accompanying photograph which shows a side perspective view of the flowers. The photograph is of a 25-week-old plant grown in an outdoor environment in Stuttgart, Germany in June 2021.

The colors shown are as true as can be reasonably obtained by conventional photographic procedures.

DESCRIPTION OF THE NEW VARIETY

The following detailed descriptions set forth the distinctive characteristics of 'KLESG22041'. The data which define these characteristics were collected from asexual reproductions carried out in Stuttgart, Germany. Data was collected on 7-week-old plants from potting grown in a foil house where no plant regulators were used, in Stuttgart, Germany in April 2023. Color references are to the R.H.S. Mini Colour Chart of The Royal Horticultural Society of London (R.H.S.), (2005).

Classification:
- *Family.*—Scrophulariaceae.
- *Botanical.*—*Sutera grandiflora.*
- *Common.*—*Sutera.*
- *Designation.*—'KLESG22041'.

Parentage:
- *Female parent.*—Proprietary *Sutera* line 'SG-2016-0652' (unpatented).
- *Male parent.*—Proprietary *Sutera* line 'SG-2016-0692' (unpatented).

Plant:
- *Habit.*—Trailing and flat.
- *Height.*—4.0 cm.
- *Spread.*—22.0 cm.
- *Life cycle.*—Blooms from spring until September.
- *Form.*—Trailing and round.
- *Time to produce a rooted cutting.*—3 weeks.
- *Time to bloom from propagation.*—Finished product could be observed after 5-6 weeks after potting.
- *Lastingness of inflorescence on the plant.*—About 7 days.
- *Rooting habit.*—Fine, fibrous roots.
- *Root color.*—White to cream white (RHS 155C), getting brown if too wet.

Stems:

*Number of stems per plant.*—5 main shoots with side shoots.

*Length.*—About 11.0 cm.

*Diameter.*—0.4 cm.

*Internode length.*—2.0 cm.

*Color.*—RHS 144C.

*Texture.*—Pubescence.

*Anthocyanin.*—Absent.

Leaves:

*Arrangement.*—Single, opposite.

*Type.*—Simple.

*Number of leaves per branch.*—7 pairs, without side shoots and leaves.

*Shape.*—Ovate.

*Variegation.*—Absent.

*Apex.*—Acuminate.

*Base.*—Cordate.

*Margin.*—Serrate.

*Length.*—Between 1.0 cm to 3.5 cm.

*Width.*—Between 0.6 cm and 3.0 cm.

*Color.*—Immature leaf: Upper surface: RHS 138A. Lower surface: RHS 138A. Mature leaf: Upper surface: RHS 139A. Lower surface: RHS 138A.

*Texture.*—Both upper and lower surfaces: Leathery. Venation type: Pinnate. Venation color: Immature leaf: Upper surface: RHS 138A. Lower surface: RHS 138A. Mature leaf: Upper surface: RHS 139A. Lower surface: RHS 138A.

*Petiole.*—Length: Immature leaf: 0.05 cm. Mature leaf: 0.5 cm. Diameter: 0.2 cm. Texture: Pubescence. Color: Immature leaf: RHS 138A. Mature leaf: RHS 139A.

Inflorescence:

*Blooming habit.*—Freely flowering.

*Quantity of inflorescence per stem.*—5.

*Type of inflorescence.*—Single, salverform flowers.

*Persistent or self-cleaning flower.*—Self-cleaning flower.

*Fragrance.*—Present but only foliage not flowers.

Peduncle:

*Length.*—1.2 cm.

*Diameter.*—0.1 cm.

*Color.*—RHS 138A.

*Texture.*—Pubescence.

*Strength.*—Thin.

Bud:

*Shape.*—Tubular.

*Diameter.*—0.6 cm.

*Length.*—0.7 cm.

*Color (at tight bud).*—RHS 145C and later on RHS 83B.

Corolla (flower):

*Type and shape.*—Single-type, nearly round, lower part tube and funnel.

*Corolla, horizontal diameter.*—3.0 cm.

*Corolla, total length.*—1.2 cm. Color of throat: Inner surface: RHS 13A. Outer surface: RHS 145D.

*Tube/funnel.*—Length (cm): 1.1 cm. Diameter (cm): 0.3 cm. Texture of funnel: Inner surface: Leathery. Outer surface: Leathery.

Petal (lobes):

*Length.*—3.0 cm.

*Width.*—3.0 cm.

*Apex.*—Rounded tips.

*Base.*—Fused to a tube.

*Margin.*—Entire.

*Color.*—Inner surface: RHS 82A, base of the lobes the coloration is getting darker to RHS 80A, this darker color is strongly depending on heat and light conditions. Outer surface: RHS 82B, base of the lobes the coloration is getting darker to RHS 80A, this darker color is strongly depending on heat and light conditions.

*Texture.*—Upper surface: Leathery. Lower surface: Leathery.

Calyx:

*Arrangement and appearance.*—Whorl of 5 sepals surrounding the base of the flower tube, sepals are fused at the base.

*Sepals.*—Color: Upper surface: RHS 137C. Lower surface: RHS 137C. Length: 1.0 cm. Width: 0.1 cm. Apex: Acuminate. Base: Fused. Margin: Entire. Texture: Upper surface: Pubescence. Lower surface: Pubescence.

Reproductive organs:

*Stamens.*—Quantity: 4. Filament: Color: RHS 145D. Length: 1.1 cm. Diameter: 0.1 cm. Anther color: RHS 14B. Pollen amount: Moderate. Pollen color: RHS 13A.

*Pistil.*—Quantity per flower: 1. Length: 1.1 cm. Stigma color: RHS 145B. Style color: RHS 145B. Style length: 1.0 cm. Ovary color: RHS 145B.

Fruit and seed set: None observed.

Disease and pest/insect resistance: None observed.

COMPARISON WITH PARENTAL LINES AND KNOWN VARIETY

'KLESG22041' is a distinct variety of *Sutera* having a pink flower color; 'KLESG22041' is distinguished from its parents as described in Table 1:

TABLE 1

Comparison with Parental Lines

| Trait | Variety 'KLESG22041' | Female parent 'SG-2016-0652' | Male parent 'SG-2016-0692' |
|---|---|---|---|
| Color of flower | Pink | Light pink | Pink |
| Flower size | Large | Large | Medium |

'KLESG22041' is most similar to the *Sutera* plant named Scopia® 'Gulliver Rose'. Differences between the two varieties are described in Table 2:

TABLE 2

Comparison with Similar Variety

| Trait | Variety 'KLESG22041' | Commercial line Scopia ® 'Gulliver Rose' (unpatented) |
|---|---|---|
| Flower size | Bigger flowers than Scopia ® 'Gulliver Rose' | Smaller flowers than 'KLESG22041' |

I claim:

1. A new and distinct cultivar of *Sutera* Plant Named 'KLESG22041' as described and illustrated herein.

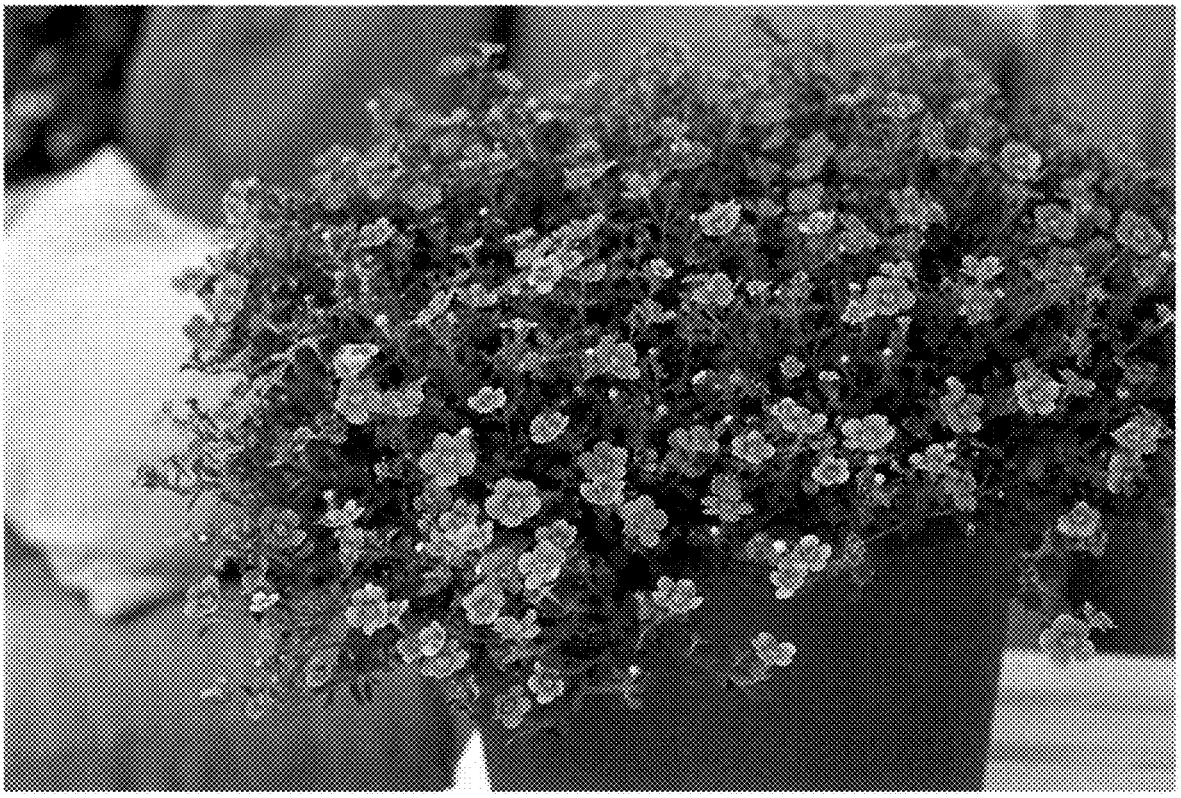

* * * * *